United States Patent [19]
Lynn

[11] Patent Number: 5,167,643
[45] Date of Patent: Dec. 1, 1992

[54] NEEDLE PROTECTION STATION

[76] Inventor: Lawrence A. Lynn, 1275 Olentangy River Rd., Suite 202, Columbus, Ohio 43212

[21] Appl. No.: 515,466

[22] Filed: Apr. 27, 1990

[51] Int. Cl.⁵ .............................................. A61M 5/00
[52] U.S. Cl. ..................................... 604/263; 604/251
[58] Field of Search .............. 604/167, 171, 268, 263, 604/192, 198, 905, 264, 251

[56] References Cited

U.S. PATENT DOCUMENTS

| | | | |
|---|---|---|---|
| 2,400,722 | 5/1946 | Swan | 604/192 X |
| 3,021,942 | 2/1962 | Hamilton | 206/365 |
| 3,893,608 | 7/1975 | Koenig | 225/1 |
| 4,248,223 | 2/1981 | Turner et al. | 604/251 X |
| 4,248,246 | 2/1981 | Ikeda | 604/263 X |
| 4,474,734 | 10/1984 | Cooper | 604/263 X |
| 4,559,042 | 12/1985 | Votel | 604/192 |
| 4,654,034 | 3/1987 | Masters | 604/192 |
| 4,735,617 | 4/1988 | Nelson et al. | 604/263 X |
| 4,740,204 | 4/1988 | Masters et al. | 604/263 X |
| 4,840,618 | 6/1989 | Marvel | 604/192 X |
| 4,852,844 | 8/1989 | Villaveces | 604/263 X |
| 4,919,656 | 4/1990 | Bracker | 604/192 |
| 4,921,489 | 5/1990 | Frizzell | 604/192 |
| 4,950,242 | 8/1990 | Alvarez | 604/192 X |

OTHER PUBLICATIONS

The Deseret Company, Sandy, Utah 84070, Product Profile, Printed in the U.S.A., form D-6395B (Apr. 1979), The Deseret Family of Intermittent Infusion Devices.

Primary Examiner—Gene Mancene
Assistant Examiner—Jeffrey A. Smith
Attorney, Agent, or Firm—Cushman, Darby & Cushman

[57] ABSTRACT

A station for temporarily housing the tip and shaft of a needle or blunt cannula within a protected environment in which an elastomeric core extends into a bore formed in a housing having a tubular shape. An integral shield extends outwardly from the tubular housing between proximal and distal ends and protects the fingers during use. The portion of the housing between the closed end and the shield serves as a handle. Preferably the elastomeric core and housing are molded together by insert or core molding.

38 Claims, 4 Drawing Sheets

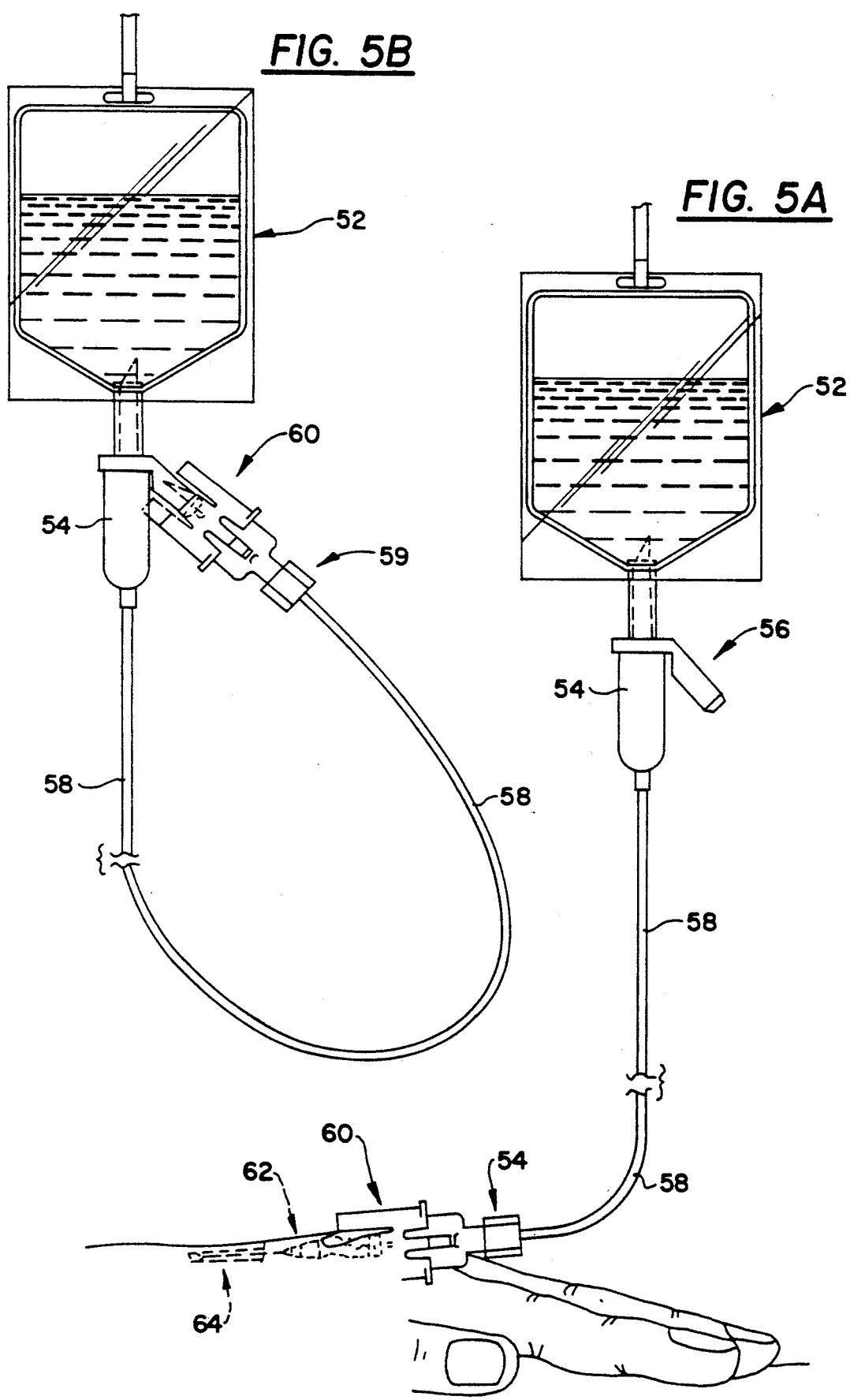

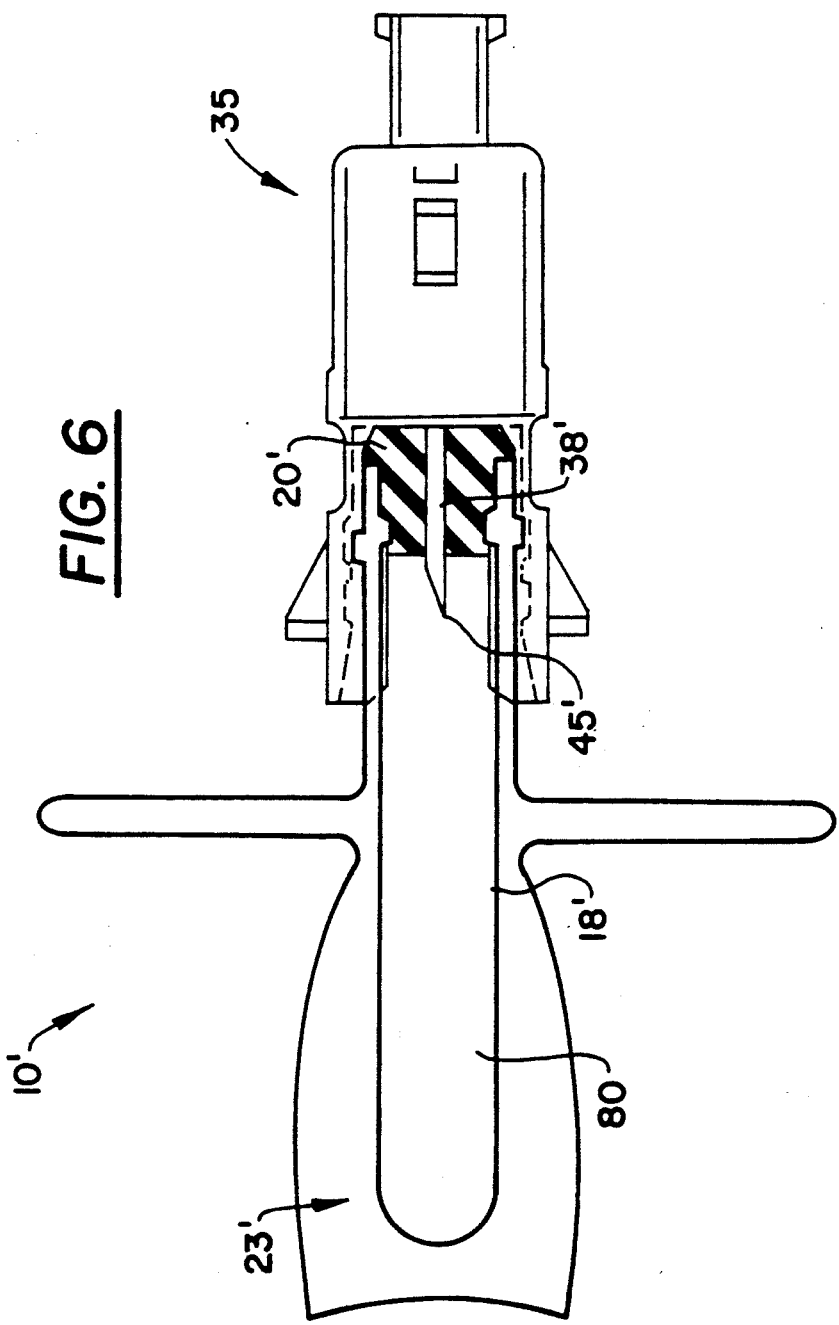

NEEDLE PROTECTION STATION

BACKGROUND AND FIELD OF INVENTION

This invention relates to a novel, reusable medical needle protection station.

The risk of needlestick transmitted infection to hospital personnel is well known. Conventional needles are now universally provided by their manufacturers with a snap on or threaded on hollow cap which is removed just prior to use. A common area wherein needlestick injuries occur is in handling needles after they are temporarily or permanently withdrawn from fluid connection with a patient. In particular, the recapping of needles poses a high risk of needlestick and is now considered a violation of universal precautions and is prohibited by OSHA in the hospital environment.

Unfortunately, it is very difficult for the nurse to deal with the exposed needle after use if the nurse can not cap it. Ideally, the nurse would immediately drop this exposed and contaminated needle into a waste receptacle for disposal. However, such receptacles are not always in close proximity to the nurse at the time of the needle withdrawal and therefore the nurse often has to lay the needle on a table or hold the needle in one hand while she finishes the task at hand. During this time, the nurse is potentially exposed to needlestick risk, as are any other hospital personnel who may come into contact with the needle if it is displaced from the table and becomes lost in a bedsheet or is otherwise contacted. Despite the fact that recapping is forbidden it is in fact a common procedure for the simple reason that no practical alternative is available.

In addition to the needlestick risk to hospital personnel of recapping, the needle itself may become contaminated with microorganisms during recapping. As the nurse begins to recap the needle, the tip of the needle can easily contact the side of the cap potentially resulting in contamination. In addition, unless the nurse uses a new cap from a sterile package each time the needle is recapped, the original cap is potentially contaminated if the hollow interior of the cap has been exposed to the ambient nonsterile environment for an significant length of time.

Thus, in the administration of piggyback medications, if the nurse chooses to recap, the nurse should use a new cap, each from their own separate sterile package. Indeed, due to the risk of injury of hospital personnel all authorities presently recommend that an entire new needle and cap be utilized each time a piggyback medication is given to a patient despite the additional expense and time required. For economic and practical reasons that procedure often is not followed.

The universal coupler of my pending application Ser. No. 07/509,638 filed Apr. 17, 1990 (the disclosure of which is hereby incorporated by reference) makes recapping without risk of infection to hospital personnel possible because the invention is configured so as to inhibit the digit of the human hand from entering the space which contains the needle. However, even with use of this coupler the other aforementioned problems relative to capping would still exist. In particular, there remains the problem of the interior of caps becoming contaminated after they have been removed from the needle. Therefore, the nurse, to be completely safe, must obtain a new cap each time she recaps my universal connector if the interior of the previous cap has been exposed to the ambient environment for a substantial period of time.

Blunt needles and cannula are now being used in place of the conventional sharp needle because the risk of such a blunt tip piercing the skin is remote. However, the contamination problem with microorganisms during recapping discussed above is still present with these devices.

SUMMARY OF INVENTION

The present invention comprises a novel, reusable, sterile, sealed needle or cannula protection station. This device provides a reusable means for the maintenance of needle sterility on an intermittent basis and obviates the need for conventional caps. The needle can be "docked" or "minded" at the station during times it is not in use and this reuse and redocking of the needle can potentially continue for as long as 72 hours.

The sterility protection station comprises, in general, a housing having a sterile internal bore, a proximal end, and a distal end. The housing is preferably comprised of relatively hard plastic and is impenetrable even by a sharp steel needle. The distal end is sealed by a sterile elastomeric member which can be pierced by a needle or cannula. The elastomeric member further reseals after removal of a needle or cannula to maintain the sterility of the bore and is preferably formed as a core extending along the length of the bore. The proximal end of the housing is occluded such that the housing forms a fully enclosed tube with the internal bore being proximally dead ended. The proximal dead end is preferably comprised of substantially impenetrable, hard plastic integral with the housing.

A finger shied is preferably provided which is located intermediate the distal and proximal ends of the tube. The transverse width of the housing proximal to the shield is preferably of a diameter which allows the housing to be comfortably held by the thumb and index finger. The portion of the housing proximal to the shield therefore provides a handle for holding the protection station. The shield preferably is comprised of a substantially planner member of hard plastic and protects the fingers holding the handle should the needle slip during insertion into the elastomeric sealing member. The transverse width of the shied is preferably at least two times the diameter of the housing. The shield may be substantially a flat disc extending circumferentially around the housing. Alternatively, the shield may extend in a distal or proximal direction about the housing.

The portion of the housing distal to the shield preferably is formed as a cylindrical tube. The distal end of the tube is occluded by the aforesaid sealing member. A annular detent on the exterior of the tube is preferably provided intermediate the shield and the distal end of the tube for engaging a similar detent when the station is used with my universal connector or with other shrouded devices having detents. The diameter of the tube, the length of the tube distal to the shield, and the distance of the annular detent from the distal end of the tube are preferably matched to allow an optimal interface with the universal connector of my above mentioned patent application as will be described.

The protection station may be free standing and enclosed in a sealed, sterile envelope and individually packaged. Alternatively, the protector may be attached to and comprise an integral part of a secondary intravenous tubing system. For example the station could be formed a part of another molded component such as a flow drip chamber on a secondary intravenous tubing set so that it is always immediately available to the nurse using the set.

In operation, the nurse removes the station from its sterile package by grasping the handle with the thumb and index finger proximal to the shield while holding a needle such as the type enclosed within the connector of my previous application or any other needle or cannula in the other hand. The needle is then inserted into the sterile elastomeric member so that both the needle tip and needle shaft are enclosed within the sterile, dead ended bore. This protects and shields the needle tip and shaft within the sterile and sealed bore of the station. The needle can then be retained within the station until it is again ready for use. When the nurse wishes to reuse the needle the nurse withdraws it from the protection station. Upon withdrawal of the needle, the elastomeric member reseals the original perforation which was caused by the indwelling needle so that the interior of the bore remains sterile for reuse.

During use or when awaiting use, free standing stations may be hung from IV tubing by inserting the IV tubing into notches provided on the shield. Alternatively, the nurse may simply leave the station on a nearby table. When the nurse has finished using the needle and wishes to store the needle in a sterile environment for reuse later, the nurse again grabs the handle of the station with her thumb and index finger and prepares the exposed end of the elastomeric member with alcohol or other suitable antiseptic to cleanse its surface. The nurse then reinserts the needle into the elastomeric member so that the tip and at east a substantial portion shaft of the needle are again enclosed and protected within the sterile bore of the station.

Preferably the entire formerly exposed shaft of the needle is received and protected by the elastomeric member. The elastomeric member preferably extends along the length of the bore so that the needle tip remains within the elastomeric member when the needle is fully advanced. This assures that the needle is occluded at its tip so that substantial fluid from the needle cannot flow from the needle tip into the bore of the station. The station is preferably sized such that the length of the bore which receives the needle is matched with the length of needles intended for use with the station. The stations may be colored or otherwise coded to indicate the longest needle they can fully accommodate. Therefore, the nurse can advance the needle along the entire length of the needle shaft until the distal end of the needle hub abuts the exposed end of the elastomeric member. In this way, the entire length of the needle is protected in a sterile environment and the needle is "minded" for future use. It is intended that a sterile needle may be repetitively reused and stored in this way for up to 72 hours before it is discarded.

The device, therefore, provides a self-sealing, sterile, fully enclosed, needle protection station which can be prepared with antiseptic each time before use. The preferred embodiment both seals the needle at its tip and maintains sterility of the entire length of the needle shaft distal to the hub when the needle is not in use.

BRIEF DESCRIPTION OF THE DRAWINGS

FIG. 2 shows a top plan view of the embodiment of FIG. 1a.

FIG. 5a shows the secondary intravenous tubing set of FIG. 4 connected to a primary intravenous system within the vein of a patient by the connector of my previous invention.

FIG. 5b shows the connector of FIG. 5b docked at the protection station and awaiting reuse.

FIG. 6 shows an embodiment wherein the bore is partially hollow.

DESCRIPTION OF THE PREFERRED EMBODIMENT

Figure 1A:
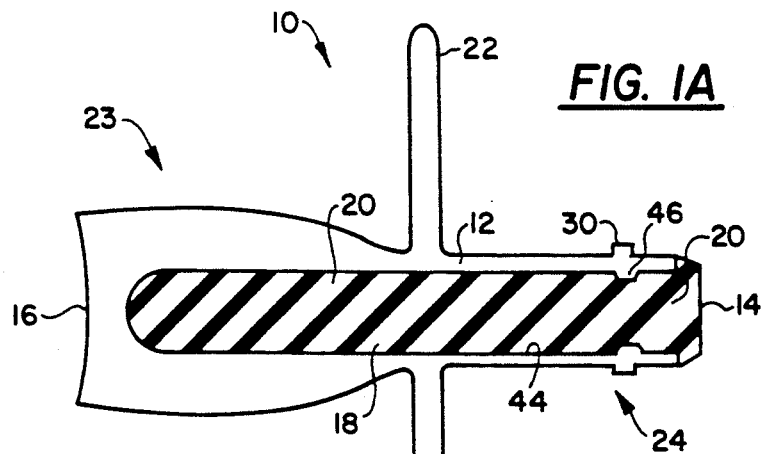
FIG. 1a shows a longitudinal sectional view of one embodiment.
Figure 1B:
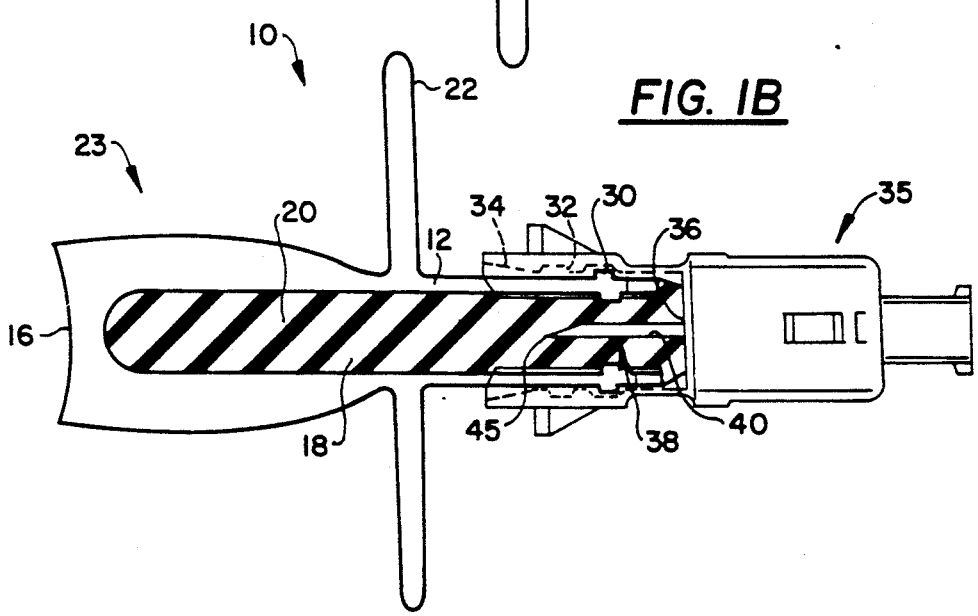
FIG. 1b shows the section view of FIG. 1a with the needle universal connector of my pending patent application Ser. No. 07/509,638 received into the station.
Figure 2:
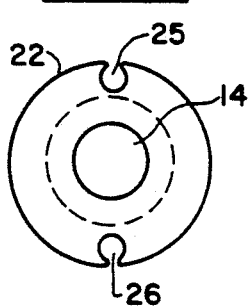
Figure 3:
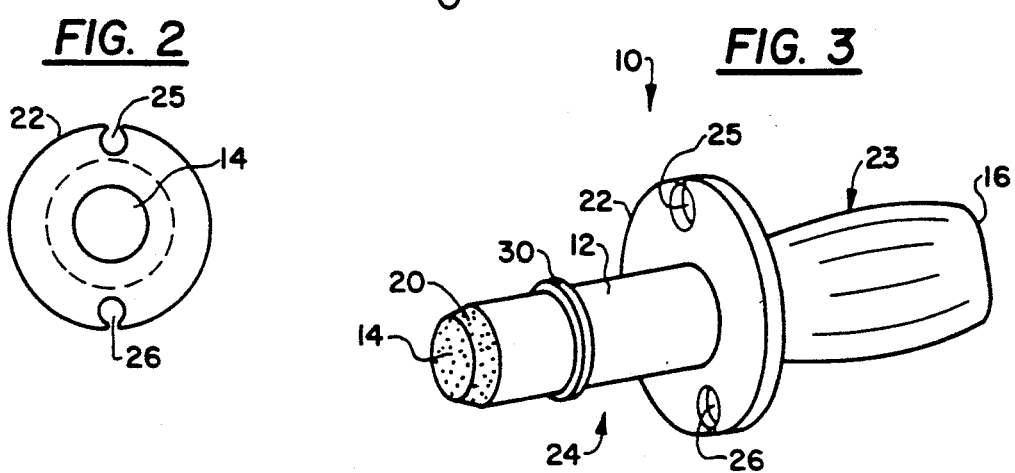
FIG. 3 shows a perspective view of the embodiment of FIGS. 1a and 2.

Reference is now made to a first embodiment of the protection station 10 shown in FIGS. 1 through 3. Housing 12 is provided with a distal end 14 and a dead-ended proximal end 16 and an internal bore 18 extending from the distal end toward the proximal end. An elastomeric sealing member 20 is provided at the distal end 14 of the bore 18 and extends into bore 18 in the direction of the proximal end 16 of the housing 12. Preferably elastomeric member 20 extends to a position adjacent the closed proximal end 16 of housing 12. An integral finger shield 22 is provided intermediate the proximal and distal ends 14 and 16 of the housing 12 effectively dividing the housing into a handle portion 23 and distal tube 24. The handle portion 23 is preferably at least 1.5 cm and the distal tube at least 1 cm in length.

As can best be seen in FIG. 2, Shield 22 has a pair of notches 25 and 26 each having a pincer-like configuration. Any suitable number of notches can be provided. These notches are sized so that a conventional intravenous tube can be squeezed past the pincers into the notch and tightly held by the notch so that the station can be, in effect, detachably hung to conventional intravenous tubing at any point along its length.

The shield 22 diameter is preferably at least two times greater than the maximum width of the handle 23 so that adequate finger protection is provided during operation. An annular detent 30 is provided on housing 12 intermediate shield 22 and the distal end 14. As shown in FIG. 1b, detent 30 is positioned so that a finger detent 32 on the interior wall of fingers 34 on the a connector 35, is positioned on the proximal side of the housing detent 30 and abutting the housing detent 30. The detent 30 is spaced from the distal end 14 of housing 12 at a distance which is slightly less than the distance from the detent 32 on the interior wall of the fingers 34 to the septum stop 36. Therefore, when the needle 38 is completely advanced so that the previously exposed shaft 40 of the needle 38 is completely within elastomeric member 20, the detent 32 of the internal wall of the fingers 34 is slightly distal to housing detent 30. This allows the station 10 to be securely held by the detents 30 and 32 in a position wherein the formerly exposed needle shaft 40 and tip 45 are completely covered by the elastomeric member 20 and the tip 45 is occluded by member 20.

Preferably the elastomeric member 20 and housing 12 are insert molded together. The interior surface 44 of housing 12 is provided with an inwardly protruding extension 46 for fixing the elastomeric member 20 in pace within the bore 18. Elastomeric member 20 further extends beyond the distal end 14 of housing 12 to aid in optimal preparation with antiseptic.

Figure 4:
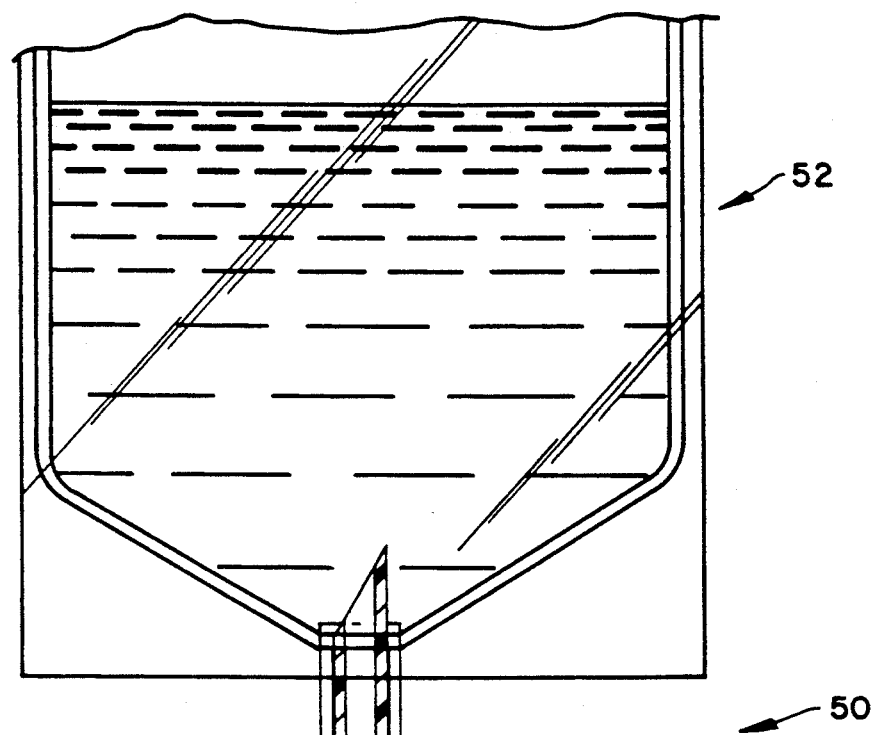
FIG. 4 shows a portion of a secondary intravenous tubing system having an integral station and drip chamber.

In a modification, as shown in FIGS. 4 and 5, the station can be molded as an integral portion of a secondary intravenous tubing system 50. FIG. 4 shows a fluid source such as a bag of intravenous fluid 52 connected to a drip chamber 54 having an integral station 56 extending downward away from drip chamber 54. FIG. 5a shows the intravenous tube or conduit segment 58 of system 50 attached at its open distal end 59 to connector 60 which is in turn connected to a primary intravenous system 62 and catheter 64 with the vein of a patient. In this embodiment, station 56 is fixed in a position along the proximal one half of the length of a secondary intravenous set so that the intravenous tubing can be easily folded back upon itself and distally connected to the station for storage as in FIG. 5b. In another modification as shown in FIG. 6 a free standing station 10' is shown having shortened elastomeric member 20' within bore 18'. Bore 18' extends proximal to elastomeric member 20' producing a dead ended chamber 80 within a hollow handle 23'. Needle tip 45' of needle 38' is shown within chamber 80. The remainder of the structure is similar to the structure of FIGS. 1-3.

One of the primary advantages of the present invention is that it is reusable without losing sterility. However, if a user wants to discard after a single use, the simplicity and low cost of this invention make that practical. It is of course possible that, for certain patients, single use may be desirable.

Many changes and modifications can of course be carried out without departing from the spirit of the invention. The chamber 80 could be filled with a sterilizing solution such as alcohol. Further, if desired, for use with blunt cannulas, the elastomeric member may have a centrally positioned perforation extending along its longitudinal axis for receiving a blunt cannula or needle. Accordingly, the claims which follow are intended to define the invention.

What is claimed is:

1. A docking station for selectively receiving and maintaining the sterility of a fluid delivery cannula when said cannula is free from fluid communication with a patient's vasculature, including a housing having side walls, a longitudinal axis, and first and second longitudinal ends, a transverse wall spaced from said second longitudinal end of said housing, and a penetrable seal mounted to said second longitudinal end and having an exposed outer surface, said exposed outer surface being substantially free from enclosure, a cannula receiving compartment being defined by said side walls, said transverse wall and said seal, said seal being selectively penetrable by a cannula so that the cannula is at least partially received in said cannula receiving compartment, said housing defining a handle means adjacent said first longitudinal end by which said housing can be gripped and held during insertion and removal of said cannula from said seal and said housing, and further comprising shield means defined intermediate said first and second longitudinal ends for shielding a user's hand and fingers from unintentional contact with said cannula prior to proper insertion through the seal, whereby the exposed outer surface of said seal can be easily and repetitively wiped with an anti-microbial or antiseptic solution and a fluid delivery cannula which has been disengaged from fluid communication with a patient's vasculature can be repetitively inserted into said cannula receiving compartment through said seal to maintain the sterility thereof during periods of non-use.

2. A docking station as in claim 1, wherein said transverse wall is impenetrable.

3. A docking station as in claim 1, wherein said transverse wall is at said first longitudinal end of said housing.

4. A docking station as in claim 1, wherein said fluid delivery cannula comprises a needle and said seal is selectively pierceable by said needle.

5. A docking station as in claim 1, wherein said seal extends axially at lest partially into said cannula receiving compartment.

6. A docking station as in claim 1, further comprising means for coupling said housing to an intravenous fluid delivery system.

7. A docking station as in claim 6, wherein said means for coupling comprise means for detachably coupling to a length of flexible tubing.

8. A docking station as in claim 1, further including a fluid delivery system coupling assembly.

9. A docking station as in claim 1, wherein said housing defines a handle means adjacent said first longitudinal end by which said housing can be gripped and held during insertion and removal of said cannula from said seal and further comprising a radially outwardly extending shield positioned on said housing intermediate said first and second longitudinal ends.

10. A docking station as in claim 1, wherein said receiving compartment has a length sufficient to receive the entire length of said cannula inserted through said seal.

11. A docking station as in claim 1, further comprising means for coupling said housing to an intravenous fluid delivery system.

12. A docking station as in claim 11, wherein said shield means comprises a flange element projecting radially outwardly from said side walls of said housing and wherein said means for coupling comprise at least one cutout defined in said flange element for releasably engaging a length flexible tubing.

13. A docking station as in claim 12, wherein there are two, diametrically opposed cutouts defined in said flange element.

14. A docking station as in claim 1, wherein said shield means comprises a flange element projecting radially outwardly from said side walls of said housing.

15. A docking station as in claim 14, wherein said flange element has a diameter at least two times greater than a maximum diameter of said housing.

16. A secondary intravenous tubing system for alternatively connecting an intravenous fluid source to a primary intravenous tubing system or connecting an intravenous fluid source to a completely enclosed and sealed station, the system comprising:

a) a drip chamber having a spike at a first end for connection to said source of intravenous fluid, b) a flexible intravenous conduit segment having a first end and a second end extending distally from the drip chamber to said first end of said conduit, said first end of said conduit being coupled to a rigid cannula means for fluid connection to said primary system, the cannula means having a tip and a shaft and a bore extending therethrough, the system further having an open flow channel from said first end of said drip chamber to said tip of said cannula, c) a sterility protection station for repetitively receiving and maintaining the sterility of said tip and shaft of said cannula means when said cannula means is free from connection to said primary system, the station having a housing, the housing having an open distal end and a closed proximal end, and a bore extending from said open distal end to a dead end proximal to said proximal end of said housing, said station being attached to said system, and d) an elastomeric member sealing said bore of said housing near said open distal end of said housing, said elastomeric member having an exposed outer surface, said exposed outer surface being substantially free from enclosure so that the exposed outer surface can be easily and repetitively wiped with an anti-microbial or antiseptic solution, said elastomeric member receiving said cannula means when said cannula means is inserted into said bore of said housing, said elastomeric member resealing said bore of said housing when said cannula means is removed from said bore.

17. The system of claim 16 wherein said system is occluded near said tip of said cannula means when said cannula means is maximally advanced into said station.

18. The system of claim 16 wherein said station and said drip chamber are integral.

19. The system of claim 16 where said station is attached along the flexible conduit segment nearer the second end of said conduit segment than the first end of said conduit segment.

20. The system of claim 16 wherein said cannula means is a needle having a sharp tip.

21. The system of claim 16 wherein fluid flow from said fluid source out of said cannula tip is prevented by said dead end of the bore of the station.

22. The system of claim 16 wherein fluid flow from said fluid source out of said cannula tip is prevented by said elastomeric member blocking said flow from said cannula tip.

23. A fluid delivery system comprising:
an elongated flexible conduit having first and second longitudinal ends,
first means mounted to said first longitudinal end for fluidly coupling said conduit to a fluid container,
second means mounted to said second longitudinal end for fluidly coupling said conduit to a patient to allow fluid delivery through said conduit to said patient, said second means for coupling including a cannula; and
a docking station for selectively receiving and maintaining the sterility of the cannula when the cannula is decoupled from fluid communication with the patient, including:
a closed tubular housing having side walls, a longitudinal axis, first and second longitudinal ends, at least one of said ends being closed by a penetrable seal so that a cannula receiving compartment is defined by said housing and said seal, said seal being selectively penetrable by the cannula so that the cannula is at least partially received in said cannula receiving compartment, said seal having an exposed outer surface, said exposed outer surface being substantially free from enclosure so that the exposed outer surface can be easily and repetitively wiped with an anti-microbial or antiseptic solution, the second means for coupling further comprising connecting means and the docking station further comprising connecting means for engaging said connecting means of said second means for coupling to secure said second means for coupling to said station with said cannula at least partially receiving in said cannula receiving compartment.

24. A fluid delivery system as in claim 23, wherein said docking station is integral with said first means for coupling.

25. A fluid delivery system as in claim 23, wherein said cannula comprises a needle.

26. A fluid delivery system as in claim 23, wherein said other of said ends is impenetrable.

27. A fluid delivery system as in claim 23, further comprising shield means defined intermediate said first and second longitudinal ends for shielding a user's hand and fingers from unintentional contact with the cannula prior to proper insertion through the seal.

28. A fluid delivery system comprising:
an elongated flexible conduit having first and second longitudinal ends,
first means mounted to said first longitudinal end for fluidly coupling said conduit to a fluid container,
second means mounted to said second longitudinal end for fluidly coupling said conduit to a patient to allow fluid delivery through said conduit to said patient, said second means for coupling including a cannula; and
a docking station for selectively receiving and maintaining the sterility of the cannula when the cannula is decoupled from fluid communication with the patient, including:
a closed tubular housing having side walls, a longitudinal axis, first and second longitudinal ends, at least one of said ends being closed by a penetrable seal so that a cannula receiving compartment is defined by said housing and said seal, said seal being selectively penetrable by the cannula so that the cannula is at least partially received in said cannula receiving compartment, said seal having an exposed outer surface, said exposed outer surface being substantially free from enclosure so that the exposed outer surface can be easily and repetitively wiped with an anti-microbial or antiseptic solution, said docking station being interconnected with one of said flexible conduit and said first means for coupling.

29. A fluid delivery system as in claim 28, wherein said docking station is detachably coupled to said flexible conduit.

30. The combination of a connector having a medical cannula and a station for maintaining the sterility of the cannula of that connector when said cannula is free from fluid communication with a patient's vasculature, said cannula of said connector being recessed within a space of said connector so as to be substantially inaccessible by human fingers, the connector further including space defining means having an inner and outer surface, the cannula having a bore extending therethrough from a first end connectable to a fluid conveying conduit to a second end within said space, the station comprising:

a) a housing having an open first end and a closed second end and a dead ended bore extending from said open first end toward said second end, b) sealing means for sealing said opening of said first end, said sealing means having an exposed outer surface, said exposed outer surface being substantially free from enclosure so that said exposed outer surface can be easily and repetitively wiped with an anti-microbial or antiseptic solution, said sealing means selectively receiving the second end and shaft of said cannula, c) occluding means for permanently occluding the second end of said housing, said occluding means preventing volitional opening of said housing said second end.

31. The combination as in claim 30 wherein the connector has coupling means, and the station further comprising coupling means on said housing for engaging said coupling means of said connector to hold said first end of said housing within said space.

32. A fluid delivery system comprising:
an elongated flexible conduit having first and second longitudinal ends,
first means mounted to said first longitudinal end for fluidly coupling said conduit to a fluid container,
second means mounted to said second longitudinal end for fluidly coupling said conduit to a patient to allow fluid delivery through said conduit to sad patient, said second means for coupling including a cannula; and
a docking station for selectively receiving and maintaining the sterility of the cannula when the cannula is decoupled from fluid communication with the patient, including:
a closed tubular housing having side walls, a longitudinal axis, first and second longitudinal ends, at least one of said ends being closed by a penetrable seal so that a cannula receiving compartment is defined by said housing and said seal, said seal being selectively penetrable by the cannula so that the cannula is at least partially received in said cannula receiving compartment, said seal having an exposed outer surface, said exposed outer surface being substantially free from enclosure so that the exposed outer surface can be easily and repetitively wiped with an anti-microbial or antiseptic solution, and shield means defined intermediate said first and second longitudinal ends for shielding a user's hand and fingers from unintentional contact with the cannula prior to proper insertion through the seal, said shield means comprising a flange element projecting radially outwardly from said side walls of said housing and wherein at least one cutout is defined in said shield means for releasably snugly engaging said flexible conduit to thereby couple said docking station thereto.

33. A fluid delivery system for intermittent connection to a junction terminal of a primary intravenous fluid delivery system, the primary intravenous system being in fluid communication with a patient, the system comprising:
a variable volume reservoir of fluid for administration to a patient;
en elongated conduit having first and second longitudinal ends, at least a portion of said conduit comprising a segment of flexible intravenous tubing,
first means mounted to said first longitudinal end for fluidly coupling said conduit to said reservoir,
second means mounted to said second longitudinal end for fluidly coupling said conduit to a primary intravenous system to allow fluid delivery through said conduit to a patient, said second means for coupling including a cannula, and
a docking station for selectively receiving and maintaining the sterility of the cannula when the cannula is decoupled from fluid communication with the patient, including:
a closed tubular housing having side walls, a longitudinal axis, and proximal and distal longitudinal ends, said housing being closed adjacent both said ends, at least said proximal end being closed by a penetrable seal so that a cannula receiving compartment is defined by said housing and said seal, said seal being selectively penetrable by the cannula so that the cannula is at least partially received in said cannula receiving compartment, said seal having an exposed outer surface, said exposed outer surface being substantially free from enclosure so that the exposed outer surface can be easily and repetitively wiped with an anti-microbial or antiseptic solution,
the second means for coupling further comprising connecting means and the docking station further comprising connecting means for engaging said connecting means of said second means for coupling to secure said second means for coupling to said station with said cannula at least partially received in said cannula receiving compartment.

34. The system of claim 33, wherein the docking station is positioned along a proximal half of said conduit.

35. The system of claim 34, wherein the docking station is positioned along a proximal third of said conduit.

36. The system of claim 34, wherein the docking station is configured so that said proximal end of said docking station is similar in dimensions and shape to a proximal end of a junction terminal of a primary intravenous fluid delivery system.

37. The system of claim 36, further comprising a connector disposed adjacent said cannula, the connector having means for coupling to either a junction terminal or said proximal end of said docking station when said cannula is received into the junction terminal or said docking station, respectively, the coupling means preventing inadvertent displacement of said cannula from either the junction terminal or said docking station.

38. The system of claim 33, wherein the docking station is positioned proximal to said flexible tubing.

* * * * *